United States Patent [19]

Crowl

[11] Patent Number: 4,582,800
[45] Date of Patent: Apr. 15, 1986

[54] NOVEL VECTORS AND METHOD FOR CONTROLLING INTERFERON EXPRESSION

[75] Inventor: Robert M. Crowl, Little Falls, N.J.

[73] Assignee: Hoffmann-La Roche Inc., Nutley, N.J.

[21] Appl. No.: 397,388

[22] Filed: Jul. 12, 1982

[51] Int. Cl.$^4$ ............ C12P 21/02; C12N 15/00; C12N 1/20; C12N 1/00

[52] U.S. Cl. .................. 435/70; 435/172.3; 435/253; 435/317; 435/811; 935/29; 935/41; 935/45; 935/60

[58] Field of Search ............ 435/68, 172, 253, 317, 435/70, 172.3; 935/29, 41, 45, 60

[56] References Cited

PUBLICATIONS

Derynck et al., Nature, vol. 287, pp. 193–197, Sep. 18, 1980.
Taniguchi et al., PNAS USA, vol. 77, pp. 5230–5233, Sep. 1980.
Guarente et al., Science, vol. 209, pp. 1428–1430, Sep. 19, 1980.
Gray et al., Nature, vol. 295, pp. 503–508, Feb. 11, 1982.

Primary Examiner—Alvin E. Tanenholtz
Attorney, Agent, or Firm—Jon S. Saxe; George M. Gould; William H. Epstein

[57] ABSTRACT

Improved vectors and methods for regulating the expression in bacteria of a eucaryotic anti-viral protein, such as mature human immune interferon, the gene for which has been cloned onto a bacterial plasmid, is disclosed. The improved vectors incorporate and method utilizes transcriptional regulatory elements derived from bacteriophage lambda and ribosome binding sites either derived from bacteriophage lambda and/or synthesized chemically.

15 Claims, 12 Drawing Figures

λ cI857 S$am_7$ DNA (dam⁻) – 49,000 bp

↓ *Hinf* I

Isolate 180–220 bp size class

↓ *Hae* II

Isolate 82 bp *Hinf* I–*Hae* II fragment

↓

*Hinf* I — *Mbo* I — *Hae* II

SD$_{int}$–82

*Mbo* I
↓
*Hinf* I ——————— TTTTGAAGAGGATCAGAAATG ——— *Hae* II

FIG. 4

```
                                          S1
5' ACTTCTTTGGCTTAATTCTCTCGGAAACG ATG AAA TAT ACA AGT TAT ATC TTG
                                 Met Lys Try Thr Ser Tyr Ile Leu

GCT TTT CAG CTC TGC ATC GTT TTG GGT TCT CTT GGC TGT TAC TGC CAG
                                         S20  1
Ala Phe Gln Leu Cys Ile Val Leu Gly Ser Leu Gly Cys Tyr Cys Gln

GAC CCA TAT GTA AAA GAA GCA GAA AAC CTT AAG AAA TAT TTT AAT GCA
                                                              20
Asp Pro Tyr Val Lys Glu Ala Glu Asn Leu Lys Lys Tyr Phe Asn Ala

GGT CAT TCA GAT GTA GCG GAT AAT GGA ACT CTT TTC TTA GGC ATT TTG
Gly His Ser Asp Val Ala Asp Asn Gly Thr Leu Phe Leu Gly Ile Leu

40
AAG AAT TGG AAA GAG GAG AGT GAC AGA AAA ATA ATG CAG AGC CAA ATT
Lys Asn Trp Lys Glu Glu Ser Asp Arg Lys Ile Met Gln Ser Gln Ile

60
GTC TCC TTT TAC TTC AAA CTT TTT AAA AAC TTT AAA GAT GAC CAG AGC
Val Ser Phe Tyr Phe Lys Leu Phe Lys Asn Phe Lys Asp Asp Gln Ser

80
ATC CAA AAG AGT GTG GAG ACC ATC AAG GAA GAC ATG AAT GTC AAG TTT
Ile Gln Lys Ser Val Glu Thr Ile Lys Glu Asp Met Asn Val Lys Phe

100
TTC AAT AGC AAC AAA AAG AAA CGA GAT GAC TTC GAA AAG CTG ACT AAT
Phe Asn Ser Asn Lys Lys Lys Arg Asp Asp Phe Glu Lys Leu Thr Asn

TAT TCG GTA ACT GAC TTG AAT GTC CAA CGC AAA GCA ATA CAT GAA CTC
Tyr Ser Val Thr Asp Leu Asn Val Gln Arg Lys Ala Ile His Glu Leu

120
ATC CAA GTG ATG GCT GAA CTG TCG CCA GCA GCT AAA ACA GGG AAG CGA
Ile Gln Val Met Ala Glu Leu Ser Pro Ala Ala Lys Thr Gly Lys Arg 140                         146
AAA AGG AGT CAG ATG CTG TTT CGA GGT CGA AGA GCA TCC CAG TAA TGG
Lys Arg Ser Gln Met Leu Phe Arg Gly Arg Arg Ala Ser Gln ---

TTGTCCTGCCTGCAATATTTGAATTTTAAATCTAAATCTATTTATTAATATTTAACATTATTT

ATATGGGGAATATATTTTTAGACTCATCAATCAAATAAGTATTTATAATAGCAACTTTTGTGT

AATGAAAATGAATATCTATTAATATATGTATTATTTATAATTCCTATATCCTGTGACTGTCTC

ACTTAATCCTTTGTTTTCTGACTAATTAGGCAAGGCTATGTGATTACAAGGCTTTATCTCAGG

GGCCAACTAGGCAGCCAACCTAAGCAAGATCCCATGGGTTGTGTGTTTATTTCACTTGATGAT

ACAATGAACACTTATAAGTGAAGTGATACTATCCAGTTACTGCCGGTTTGAAAATATGCCTGC

AATCTGAGCCAGTGCTTTAATGGCATGTCAGACAGAACTTGAATGTGTCAGGTGACCCTGATG

AAAACATAGCATCTCAGGAGATTTCATGCCTGGTGCTTCCAAATATTGTTGACAACTGTGACT

GTACCCAAATGGAAAGTAACTCATTTGTTAAAATTATCAATATCTAATATATATGAATAAAGT

VECTORS AND METHOD FOR CONTROLLING INTERFERON EXPRESSION

FIELD OF THE INVENTION

This invention relates to improved vectors and methods for controlling, via recombinant DNA technology, eucaryotic protein expression in transformed procaryotic cells. This invention further relates to procaryotic cells so transformed.

BACKGROUND ART

At present, it is known that various factors may effect the efficiency of expression of eucaryotic proteins whose genes have been cloned onto bacterial plasmids or expression vectors. Two of the most important factors which both define and govern this protein expression are the accuracy with which the bacterial cell transcribes the inserted gene into mRNA and the efficiency of translation of this mRNA by bacterial ribosome into protein. The efficiency of transcription and translation, generally known as expression, is believed to be dependent upon the nucleotide sequences typically situated ahead of the cloned genes on the vector DNA. These expression control sequences, in large part, comprise promoter/operator sites wherein the RNA polymerase interacts to initiate transcription and ribosome binding sites wherein the ribosomes bind and interact with the mRNA to initiate translation into protein.

The prior art has uncovered varous obstacles to expressing eucaryotic proteins whose genes have been cloned onto bacterial plasmids. For instance, the prior art has recognized that it may be both harmful to the host cell and the stability of the hostvector system if the eucaryotic protein is expressed and is present in the cell in large quantities. The prior art has also recognized that the mRNA's transcribed in a bacterial host from cloned eucaryotic DNA inserts do not possess the necessary regulatory signals, i.e., ribosome binding sites, (as do procaryotic mRNA's) for recognition by procaryotic ribosomes.

In order to overcome these potential obstacles, the prior art has attempted to alter or substitute the naturally occurring portion of the nucleotide sequences which control or regulate the transcription and/or translation process or ribosome binding process. A tailored expression control sequence, desired by the prior art, in addition to improving the efficiency of transcription and translation of the cloned genes, should also be controllable so as to modulate expression during bacterial growth. The expression control sequences preferred by the prior art to date are ones that may be selectively switched on and off. Host cells are thereby allowed to propagate without excessive build-up of gene products prior to switching on so as to promote the expression of large amounts of the desired protein products.

Various expression control sequences, different from those naturally occurring on the plasmid have, therefore, been employed by the prior art to improve control over the expression of eucaryotic proteins and polypeptides in bacterial hosts. These include, for example, utilization of the operator, promoter, ribosome binding and interaction sequences of the lactose operon of *E. coli*, the corresponding sequences of the tryptophan synthetase system of *E. coli* and the major operator and promoter regions of bacteria phage λ (a bacterial DNA virus) [H. Bernard et al., "Construction Of Plasmid Cloning Vehicles that Promote Gene Expression From The Bacteriophage Lambda $P_L$ Promoter", *Gene*, 5, pp. 59–76 (1979) said reference being incorporated by reference herein.

The $P_L$ promoter of the λ phage has been used to express eucaryotic and procaryotic proteins cloned into a procaryotic organism. The promoting activity of $P_L$ was found to be switched off at low temperature in the presence of a cI(ts) temperature sensitive gene that specifies a temperature-sensitive repressor, but could be activated by heat induction when expressing a procaryotic protein. Examples of the prior art use of this promoter system may be seen in European Patent Application 81301413.1 filed Apr. 1, 1981 and Derynck et al., "Expression of human fibroblast interferon gene in *Escherichia coli*", *Nature*, 287, 193–197 (1980). In these references, both of which are incorporated by reference herein, the $P_L$ promoter system was used in conjunction with the entire bacterial ribosome binding site in expressing eucaryotic proteins such as fibroblast interferon.

In order to express eucaryotic genes in *E. coli* the prior art has generally taken one of two approaches, both utilizing recombinant DNA techniques, so as to overcome the lack of proper regulatory signals on the eucaryotic genes: (1) inserting the eucaryotic coding sequence within the coding region of a bacterial gene, such as ⊕-lactamase; thus utilizing the entire ribosome binding site (RBS) of the *E. coli* gene, or (2) constructing a so-called "hybrid" RBS consisting of the SD sequence, the sequences proximal to the SD sequence (from the *E. coli* DNA and AUG start codon) plus the remaining coding sequence derived from the eucaryotic DNA. The SD sequence is a sequence of 3 to 9 bses which are complementary to bases at the 3'-end of 16s ribosomal RNA known as the Shine-Delgarno sequence (hence, SD) which bases are located between the promoter and initiation codon for the eucaryotic gene. One or the other of these approaches is necessary for expression of eucaryotic DNA in *E. coli* since eucaryotic genes do not contain sequences resembling the SD sequence at the start of translation.

The major disadvantage of the first approach is that it results in the production of a fusion polypeptide, that is, part of the gene product is encoded by the *E. coli* DNA and part by the eucaryotic DNA. This fusion protein may however, be processed into active form by unknown and inefficient mechanisms within the cell. The second approach has been successfully employed to produce authentic mature (complete and biologically active with no attached pre-sequence) gene products identical to those produced in the natural situation, i.e., in the eucaryotic cell. See Derom et al., "High-level synthesis in *Escherichia coli* of the SV40 small-t antigen under control of the bacteriophage lambda $P_L$ promoter", *Gene*, 17, 55–54 (1982); and Gheysen, et al., "Systematic alteration of the nucleotide sequence preceding the translation initiation codon and the effects on bacterial expression of the cloned SV40 small-t antigen gene" *Gene*, 17, 55–63 (1982) both references being incorporated by reference herein.

To date, the prior art has attempted to express various human interferon species, such as leukocyte, fibroblast and immune, with both approaches. While attempting to express fibroblast interferon (FIF), the aforementioned Gheysen et al reference utilized the first approach (wholly bacterial RBS) in conjunction with the $P_L$ promoter system. Although this reference indicates that biologically active, non-fusion proteins were obtained, it is clear that this was a result of cellular processing of fusion FIF proteins by unknown and inefficient mechanisms within the cell since the FIF gene does not have the proper translation initiation sequences. It is further apparent from this reference that the eucaryotic gene product contains the amino-acids sequence coded by the signal portion of the eucaryotic gene. Therefore, a mature form of interferon is not being expressed.

In the following references, (both being incorporated by reference herein) Gray, et al., "Expression of human immune interferon cDNA in *E. coli* amd monkey cells", *Nature*, 295, 503-508 (1982), ahd Shepard et al., "Increased Synthesis in *E. coli* of Fibroblast and Leukocyte Interferons Through Alterations in Ribosome Binding Sites" *DNA*, 1, 125-131 (1982), the "hybrid RBS" second approach was utilized. However, as noted in these references, expression was under the control of the *E. coli* trp promoter and the hybrid RBS were derived from the ATG of the eucaryotic gene and the SD and linker sequence of the trp leader. Furthermore, in both of these references the SD sequence and sequence proximal (upstream) to the SD sequence remained unchanged. The only variability introduced was into the linker region, that is a change in both number and composition of the nucleotides between the SD sequence and the ATG codon.

The prior art lacked a means for designing and constructing a hybrid ribosome binding site with the flexibility required to selectively increase expression of a cloned eucaryotic gene. Furthermore, the prior art lacked a means for controlling the expression of a cloned eucaryotic gene protein in its mature form, with a temperature sensitive promoter system and without the need for independent cellular processing of fusion proteins.

SUMMARY OF THE INVENTION

The present invention overcomes the aforementioned limitations of the prior art by providing improved vectors and methods for controlling the expression of cloned genes which code for interferon such as mature human immune interferon, in host bacterial cells.

Broadly stated, this invention comprises means for controlling the expression of the human immune interferon protein which comprises providing to a procaryotic organism the promoter and operator genes isolated from a lambda bacteriophage another gene, cI, isolated from a lambda phage which codes for a temperature sensitive (ts) repressor protein, a hybrid ribosome binding site associated with both the lambda phage promoter/operator sequences and a eucaryotic gene which codes for human immune interferon and a lysis procedure for opening the microbial cell walls so as to release the mature eucaryotic protein expressed by the organism without affecting the activity of the mature protein. Other aspects and advantages of the present invention will become apparent after reading the following specification and the adjoined claims.

BRIEF DESCRIPTION OF THE DRAWINGS

FIG. 4 illustrates the scheme used to isolate the 82 bp fragment containing the SD sequence for the int gene of bacteriophage lambda for construction of expression vector pRC15.

FIG. 10 shows the primary structure (base sequence) of the plasmid pHIT3709 as obtained in Example 5 (vii).

DETAILED DESCRIPTION OF THE INVENTION

Figure 1:
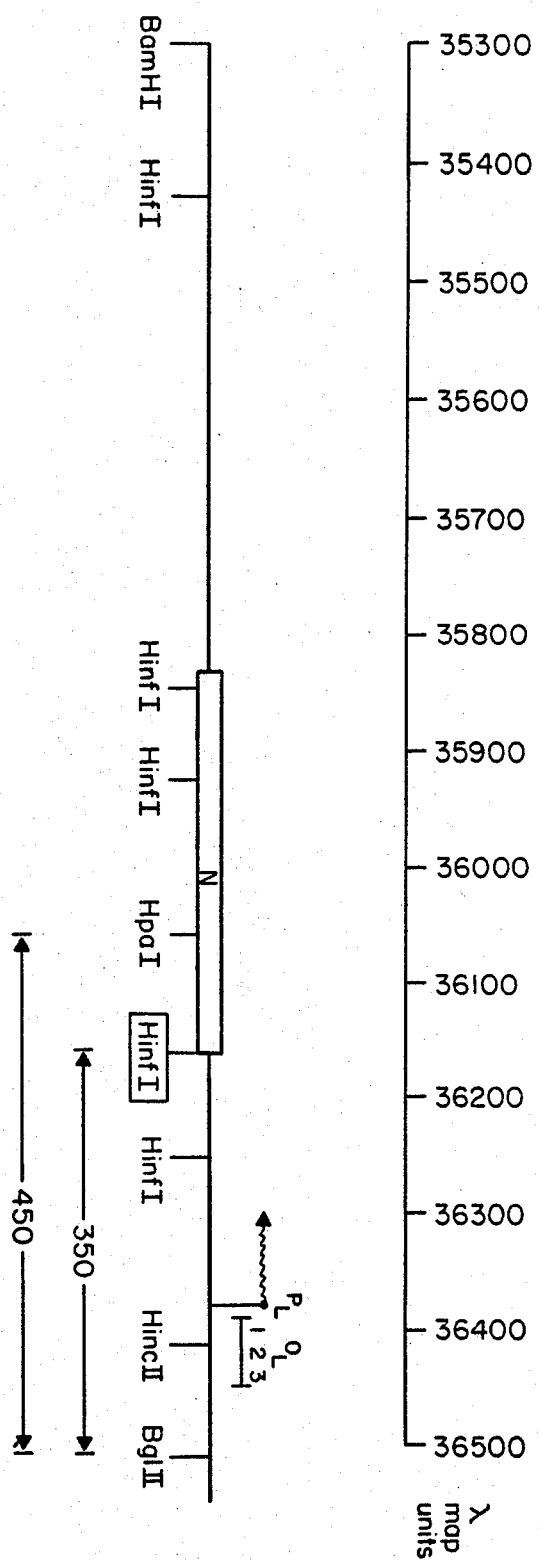
FIG. 1 is a partial restriction map of a 1200 bp Bgl II-Bam H 1 fragment containing the $P_L$ promoter.

This invention provides for an improved expression vector comprising a DNA sequence which comprises the $P_L$ promoter and $O_L$ operator derived from a bacteriophage, a hybrid ribosome binding site, the nucleotide sequence of which is different or altered from the natural sequence as found in λ bacteriophage, and a eucaryotic gene which codes for interferon, preferably human immune interferon. This invention further comprises organisms, such as *E. coli* bacteria, transformed by this vector.

This invention further includes a method for producing interferon which comprises:
(a) transforming a host organism with an expression vector comprising a $P_L$ promoter and $O_L$ operator derived from a λ bacteriophage, a hybrid ribosome binding site, and a eucaryotic gene which codes for interferon;
(b) providing the host organism with a mutant cI repressor gene, derived from λ bacteriophage, which mutant gene codes for a temperature sensitive repressor protein;
(c) cloning the transformed organism in a culture whereby it produces the interferon coded for by the expression vector of step a;
(d) lysing the organism; and
(e) recovering the interferon from the resultant lysate.

After the cloning (incubation) of step c the cells are collected by a known method and, after suspending in a buffer solution, are lysed. As used herein, the term lysing is meant to indicate a procedure for opening cellular walls of the host and which is preferably performed enzymatically, although it may also be performed ultrasonically, mechanically or by any other means known and used by those skilled in the art. It is contemplated the interferon may be recovered from the lysate by protein purification procedures known to those skilled in the art, such as by electrophoresis or chromatography (i.e., antibody affinity chromatography). The eucaryotic gene preferred in this invention codes for human immune interferon and more preferably, this interferon in its mature form. It is also an aspect of this invention that the human immune interferon is produce in its mature form and is, therefore, biologically active and without any presequence attached thereto. The immune interferon of this invention (hereinafter sometimes referred to as "IFI") is produced by immunocompetent cells under those conditions which may induce blast-formation of lymphocytes or production of lymphokines.

In order to more effectively and greater detail set forth this claimed invention, the following abbreviations will be utilized:

DNA = deoxyribonucleic acid
Thr = threonine
A = adenine
Cys = cysteine
T = thymine
Met = methionine
G = guanine
Glu = glatamic acid
U = uracil
Asp = aspartic acid
RNA = ribonucleic acid
Lys = lysine
EDTA = ethylenediamine tetraacetate
Arg = arginine
Gly = glycine
His = histidine
Ala = alanine
Phe = phenylalanine
Val = valine
Tyr = tyrosine
Leu = leucine
Trp = tryptophan
Ile = isoleucine
Pro = proline
Ser = serine
Asn = asparagine
Gln = glutamine
C = cytosine In order to more fully appreciate the claimed invention, certain important terms will be utilized throughout this specification. The term "nucleotide" as used herein is defined as a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C and uracil ("U").

The term "DNA sequence" is defined as a linear array of nucleotides connected one to the other by phosphodiester bonds between the 3' and 5' carbons of adjacent pentoses. The term "codon" as used herein represents a DNA sequence of three nucleotides (a triplet) which encodes (or "codes for"), through its template or messenger RNA ("nRNA"), an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

The human immune interferon of this invention is coded for by eucaryotic gene with the following nucleotide DNA sequence:

(5') TGT TAC TGC CAG GAC CCA TAT GTA AAA GAA
GCA GAA AAC CTT AAG AAA TAT TTT AAT GCA GGT
CAT TCA GAT GTA GCG GAT AAT GGA ACT CTT TTC
TTA GGC ATT TTG AAG AAT TGG AAA GAG GAG AGT
GAC AGA AAA ATA ATG CAG AGC CAA ATT GTC TCC
TTT TAC TTC AAA CTT TTT AAA AAC TTT AAA GAT
GAC CAG AGC ATC CAA AAG AGT GTG GAG ACC ATC
AAG GAA GAC ATG AAT GTC AAG TTT TTC AAT AGC
AAC AAA AAG AAA CGA GAT GAC TTC GAA AAG CTG
ACT AAT TAT TCG GTA ACT GAC TTG AAT GTC CAA
CGC AAA GCA ATA CAT GAA CTC ATC CAA GTG ATG
GCT GAA CTG TCG CCA GCA GCT AAA ACA GGG AAG
CGA AAA AGG AGT CAG ATG CTG TTT CGA GGT CGA
AGA GCA TCC CAG—X. (3')

wherein X is TAA, TGA or TAG. The above DNA (I) may have at the 5'-end thereof

ATG AAA TAT ACA AGT TAT ATC TTG GCT TTT     (III)
CAG CTC TGC ATC GTT TTG GGT TCT CTT GGC 3' or

ATG.     (IV)

When the DNA (I) has the DNA of formula (III) at the 5'-end, it codes not only for immune interferon polypeptide but also for the polypeptide having Met Lys Tyr Thr Ser Tyr Ile Leu Ala Phe Gln Leu Cys Ile Val Leu Gly Ser Leu Gly added to the N-terminus or a polypeptide equivalent thereto in activities, and when the DNA (I) has the DNA of formula (IV) at the 5'-end, it codes not only for immune interferon polypeptide but also for the polypeptide having Met added to the N-terminus. This immune interferon gene is preferably connected downstream on an expression vector DNA sequence from an adequate promoter and SD (Shine-Dalgarno) sequence, for introduction into an adequate host.

The above nucleotide sequence codes for the protein human immune interferon. The term protein (or polypeptide) as used herein, represents a linear array of amino acids connected one to the other by peptide bonds between the α-amino and carboxy groups of adjacent amino acids. The aforementioned nucleotide sequence may also be said to comprise a "gene" or a DNA sequence which codes through its mRNA for a sequence of amino acids characteristic of a specific polypeptide, herein the polypeptide human immune interferon.

The human immune interferon protein encoded for by the aforementioned gene and start signal (ATG) has the following sequence of amino acids:

Met Cys Tyr Cys Gln Asp Pro Tyr Val Lys Glu Ala
Glu Asn Leu Lys Lys Tyr Phe Asn Ala Gly His Ser
Asp Val Ala Asp Asn Gly Thr Leu Phe Leu Gly Ile
Leu Lys Asn Trp Lys Glu Glu Ser Asp Arg Lys Ile
Met Gln Ser Gln Ile Val Ser Phe Tyr Phe Lys Leu
Phe Lys Asn Phe Lys Asp Asp Gln Ser Ile Gln Lys
Ser Val Glu Thr Ile Lys Glu Asp Met Asn Val Lys
Phe Phe Asn Ser Asn Lys Lys Lys Arg Asp Asp Phe
Glu Lys Leu Thr Asn Tyr Ser Val Thr Asp Leu Asn
Val Gln Arg Lys Ala Ile His Glu Leu Ile Gln Val
Met Ala Glu Leu Ser Pro Ala Ala Lys Thr Gly Lys
Arg Lys Arg Ser Gln Met Leu Phe Arg Gly Arg Arg

Ala Ser Gln

It is also foreseeable that in the practice of this invention the first amino acid, Met, which is coded for by the ATG start signal, will be cleaved off by the microorganism after expression.

In a preferred embodiment of this invention, the gene which encodes for the above-mentioned protein is inserted into the DNA of a plasmid or cloning vector thereby forming a recombinant DNA sequence (a molecule consisting of segments of DNA from different genomes—the entire DNA of a cell or virus—which have been joined end-to-end outside of living cells). As utilized herein, a plasmid is nonchromosomal, double-stranded DNA sequence which is replicable when in a host cell. When the plasmid is placed within a unicellular host organism, the characteristics of that organism may be changed or "transformed" as a result of the genes present on the plasmid. For example, a plasmid carrying the gene for tetracycline resistance ($Tet^R$) transforms a cell previously sensitive to tetracycline into one which is resistant to it. A host cell transformed by a plasmid or vector is called a "transformant". In accordance with the present invention, a transformed host cell is cloned, preferably in vitro. Cloning is defined as the process of obtaining a population of organisms or DNA sequences which are derived from one such organism or sequence typically by incubating in an in vitro or in vivo culture with the cells replicating by asexual reproduction.

A plasmid, phage DNA or other DNA sequence which is able to replicate in a host cell and transform it may also be known as an expression vehicle, expression vector, or vector for the purposes of this invention. These vectors are characterized by one or a small number of endonuclease recognition or restriction sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance.

The improved expression vectors of this invention further comprise hybrid ribosome binding sites. Ribosome binding sites (RBS), from which the hybrid RBS are derived, comprise RNA sequences encoded by the DNA. RBS's are necessary for the initiation of translation in a host cell. RBS's essentially consist of (1) an ATG translation initiation codon for the amino acid methionine (all known $E.$ $coli$ gene products begin with the amino acid, methionine, which may or may not be subsequently cleaved off), (2) a sequence of 3 to 9 bases which are complementary to bases at the 3'-end of 16 s ribosomal RNA known as the Shine-Delgarno (SD) sequence [Shine, J. and Delgarno, L. $Nature$ 254, 34 (1975) incorporated by reference herein] and (3) a sequence of bases between the two known as the linker region.

For example, the sequence at the beginning of the $E.$ $coli$ lac z gene is ACAGGAA ACAGCT[ATG]—lac z. The underlined sequence is the SD sequence which is separated from the ATG by 7 bases. The length of the linker region between the SD sequence and ATG can vary for other genes from about 5 to 16 bases with a correlation between this distance and levels of protein expression. In addition, the sequence of the linker region can also significantly affect expression levels. Furthermore, nucleotides sequences in the SD sequence itself and flanking it and the ATG start codon have also been found to be important for efficient translation of an mRNA.

A preferred embodiment of this invention consists of a set of expression vectors which can be conveniently used to express authentic eucaryotic genes in $E.$ $coli.$ These vectors further comprise the feature that a number of different hybrid RBS's, can easily be constructed and tested for the purpose of achieving maximum levels of eucaryotic protein expression. In these hybrid ribosome binding sites the SD sequence linker region and or nucleotides upstream or flanking of the SD sequence are altered in number or composition (base sequence).

In a preferred embodiment of this invention, the microorganisms employed as the recipient in the transformation procedures and unless otherwise noted, is the microorganism $Escherichia$ $coli$ K-12 strain 294 as described in British Patent Publication No. 2055382A and which is incorporated by reference herein. This microorganism has been deposited with the American Type Culture Collection, ATCC Accession No. 31446, deposited Oct. 28, 1978. Furthermore, all recombinant DNA work herein was performed in compliance with applicable guidelines of the National Institutes of Health.

The invention, in its most preferred embodiments, is described with reference to $E.$ $coli,$ including not only $E.$ $coli$ K-12 strain 294, defined above, but also other known $E.$ $coli$ strains such as $E.$ $coli$ MA210 or RR1, or other microbial strains many of which are deposited and available from recognized microorganism depository institutions, such as the American Type Culture Collection (ATCC)-cf. the ATCC catalog listing.

The expression vectors of this invention are derivatives of pBR322 (see FIG. 2,5,6 and 7) containing the $P_L$ promoter isolated from bacteriophage λ DNA and inserted between the $tet^R$ and the $amp^R$ genes oriented in both directions (i.e., transcription proceeding toward the $amp^R$ gene or toward the $tet^R$). $P_L$ was the promoter of choice since it is a very strong promoter that can be efficiently and conveniently controlled by the λ cI repressor. The gene encoding the repressor carries a mutation, cIts2 or cIts857, which renders the repressor temperature-sensitive. At 30° C. the repressor functions normally, and from about 37° C. to about 42° C. it is inactivated. Thus the $P_L$ promoter is repressed (turned-off) at 30° C. and derepressed (turned-on) at 42° C. This feature is desirable herein in that the gene product of interest may be toxic to the cell or that if present in large quantity it would be detrimental to cell growth. The ability to control the $P_L$ promoter allows one to grow the culture at about 30° C. to about 36° C. without expressing the gene product and at an optimum time, shift the temperature from about 37° C. to about 42° C. to produce the desired gene product.

In addition to the $P_L$ promoter, the expression vectors of the disclosed invention comprise RBS's which contain one of at least three alterations in the:
(1) sequences proximal (upstream in 5' direction) to SD sequence
(2) SD sequence itself or
(3) the distance between the SD sequence and ATG codon All of the vectors of the disclosed invention also contain an EcoR1 restriction site distal (downstream in 3' direction) the SD sequence by 0,1, and 4 bases, providing a means of constructing different hybrid RBS's. Once the hybrid RBS is contructed using the EcoR1 site to join the $P_L$ SD sequence to the ATG coding sequence of the interferon coding gene, it can be further modified by restricting with EcoR1, filling-in the terimini with Klenow Polymerase I and joining the two resulting ends by blunt-end ligation with $T_4$ DNA ligase. The following examples serve to further illustrate the invention.

EXAMPLE 1

In order to isolate a 350 base pair (bp) fragment containing the λ $P_L$ promoter, 250 μg of λ cI857 Sam7 DNA (Miles Laboratories) was digested with restriction endonucleases BamH1 and Bgl II, and the products were separated on agarose gel by electrophoresis. A 1200 bp fragment containing the $P_L$ promoter was isolated from the gel (see FIG. 1).

This 1200 bp fragment was then digested completely with HpaI and partially digested with Hinf I and a 350 bp fragment was isolated from a 5% polyacrylamide gel electrophoresis. Digestion with HpaI eliminated 2 HinfI partial fragments of about 350 bp that would have otherwise contaminated the desired fragment.

This 350 bp fragment contains the $P_L$ promoter and the $O_L$ operates sites ($O_{L1}$, $O_{L2}$, $O_{L3}$) to which the λ cI repressor binds. The HinfI site, which occurs between the Shine-Delgerno (SD) sequence of the λ N gene and the initiating codon for the N gene (see FIGS. 1 and 2), allows for the construction of hybrid ribosome-binding sites for the purpose of expressing foreign genes in *E. coli*. This HinfI site may also be converted to an EcoR1 site.

Figure 2:
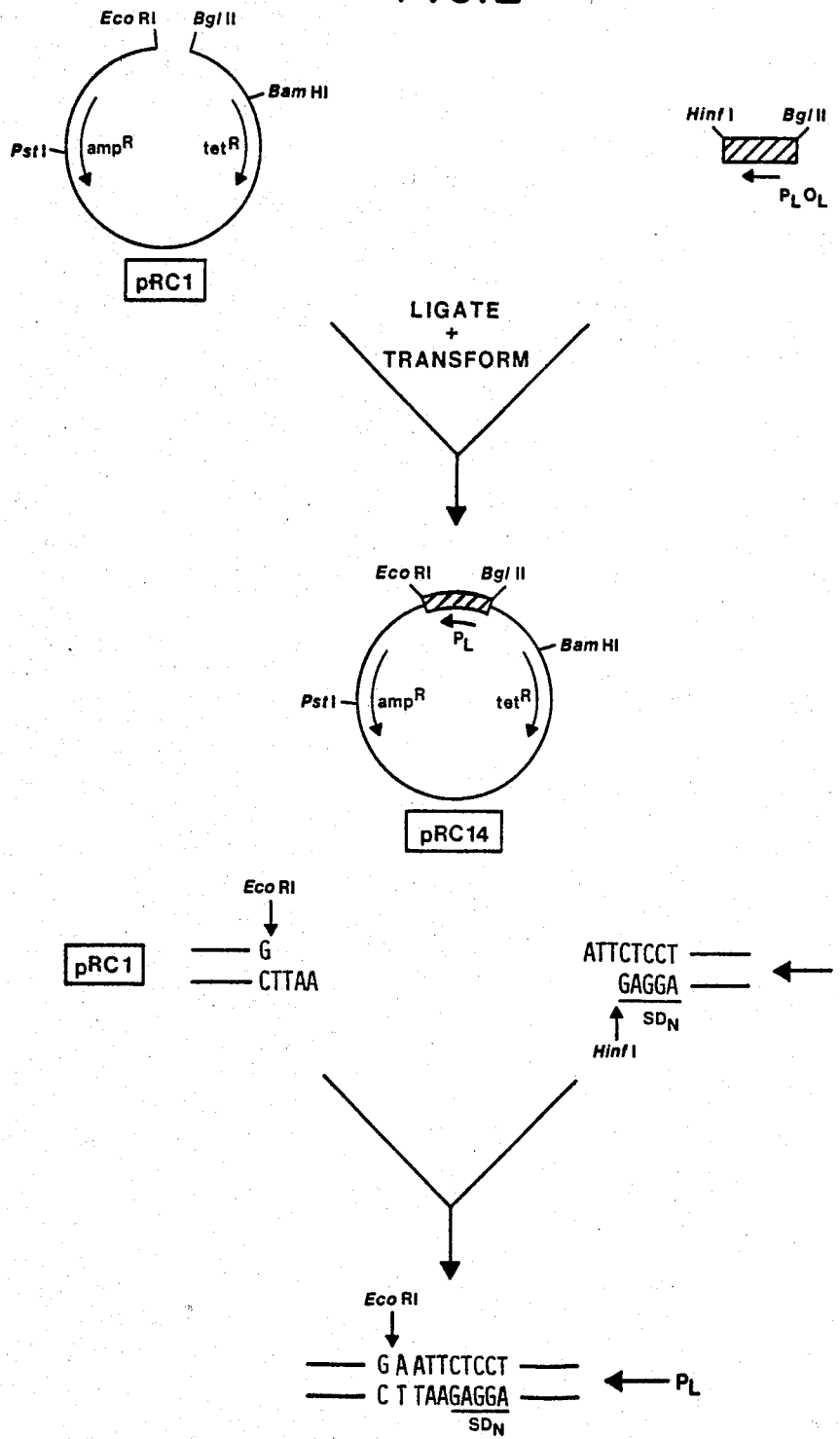
FIG. 2 illustrates the construction of expression vector pRC14 which contains the lambda $P_L$ promoter on a 350 bp insert.

The 350 bp Bgl II-HinfI fragment was cloned into plasmid pRC1 which had been digested with EcoR1 and Bgl II. pRC1 is a derivative of pBR322 that contains a Bgl II site adjacent to the EcoR1 site (see FIG. 2). FIG. 2 shows the sequences of the joining termini and indicates how the EcoR1 terminus of the vector can join to the HinfI terminus of the fragment, thus reconstituting the EcoR1 site. (The circled A in FIG. 2 was repaired by cellular mechanisms in vivo.) The resulting recombinant plasmid was designated pRC14.

Figure 7:
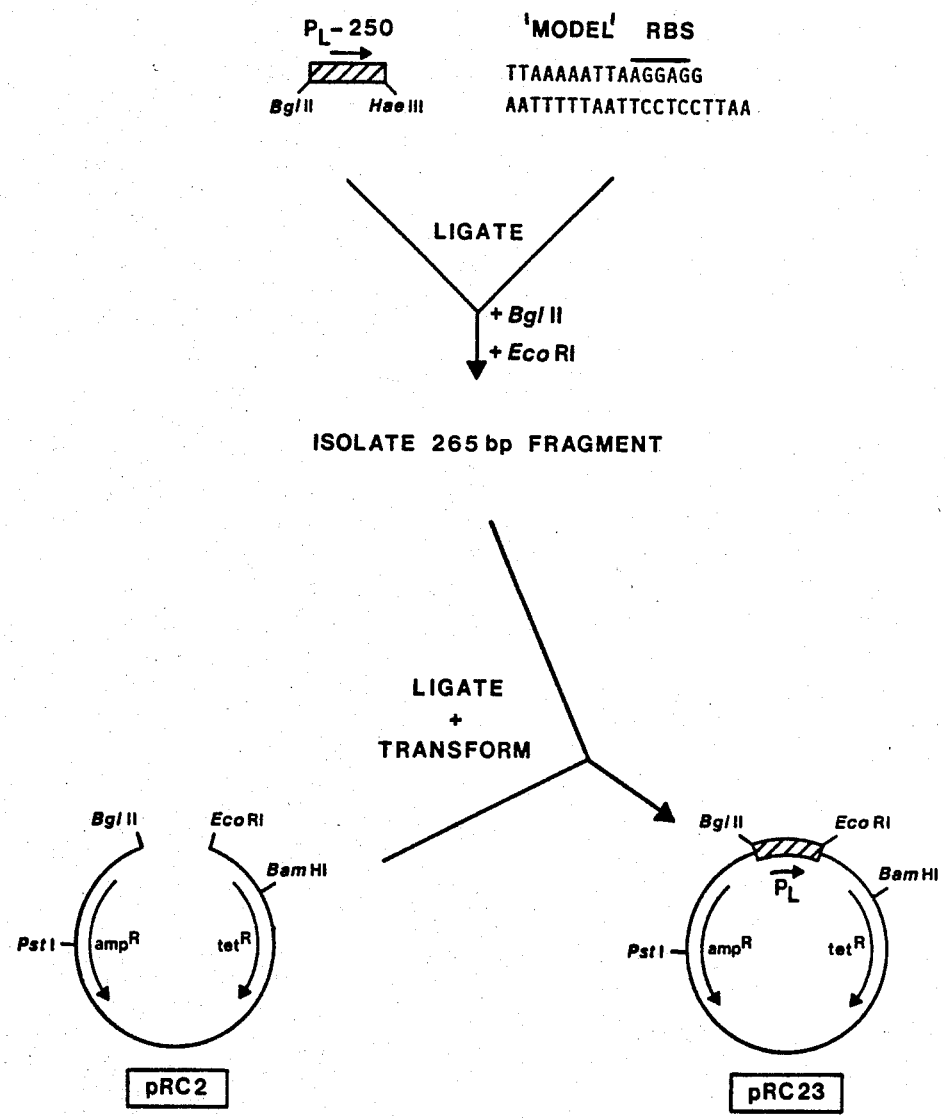
FIG. 7 illustrates the construction of expression vector pRC23 with a $P_L$ promoter and a synthetic RBS.

A number of other expression vectors using the $P_L$ promoter were also constructed (FIGS. 4,5,6 and 7). pRC15 contains, in addition to the 350 bp Bgl II-HinfI fragment described above, a 55 base pair fragment (Hinf[−MboI]) that contains the SD sequence of the λ int gene (see FIGS. 4 and 5). pRC21 and pRC22 are analogous to pRC14 and pRC15, respectively. The principle difference between these plasmids is the orientation of the inserted $P_L$-containing fragment, and thus the direction of transcription (see FIG. 5). pRC23 was constructed by ligating synthetic oligonucleotides containing a "consensus" RBS [Scherer, et al., *Nucleic Acids Research*, 8, 3895 (1980)] to a 250 bp Bgl II-Hae III fragment containing the $P_L$ promoter, and inserting the ligation product into pRC2 as shown in FIG. 7.

EXAMPLE 2

Figure 3:
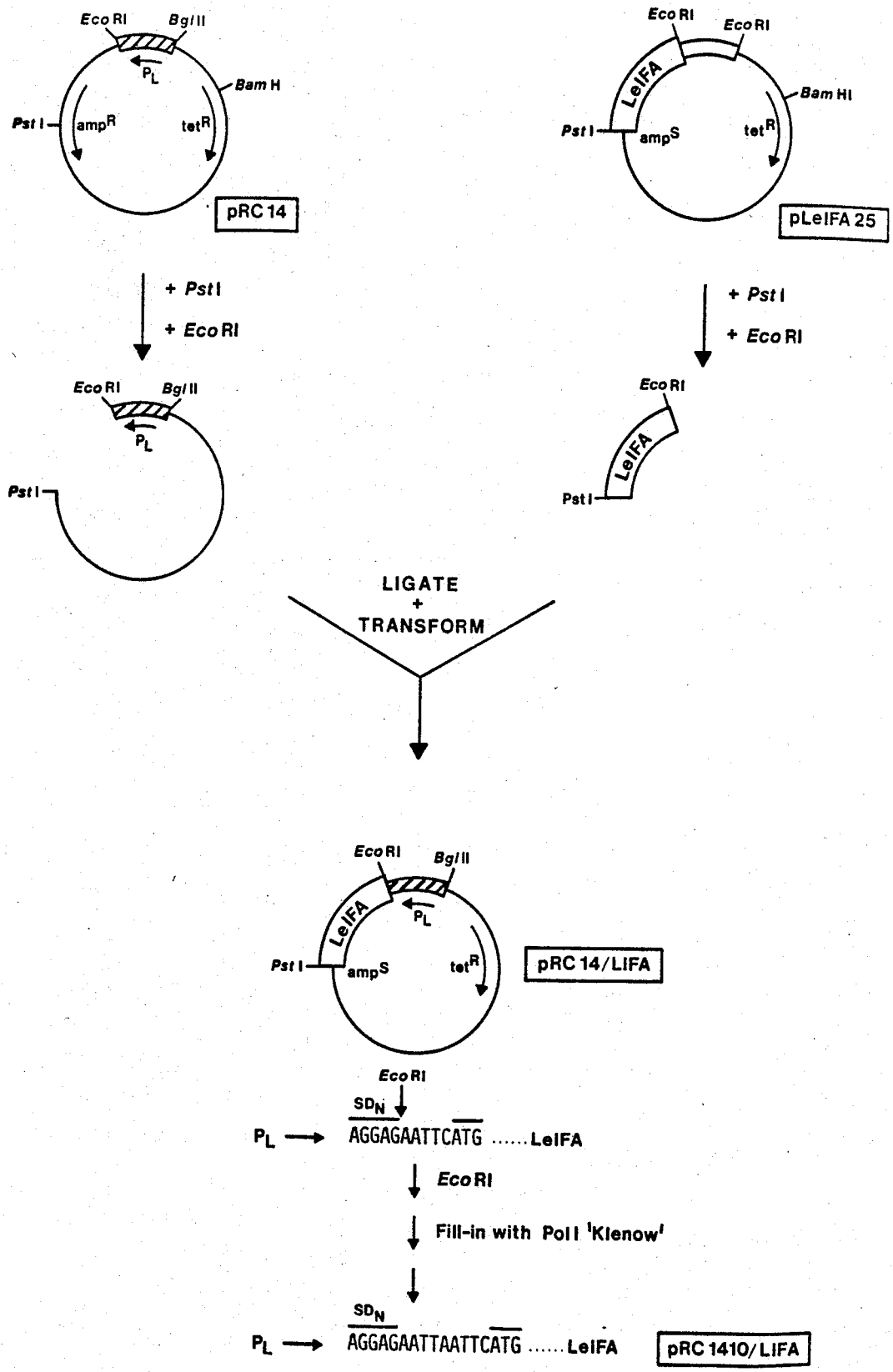
FIG. 3 illustrates leucocyte interferon gene insertion into the expression vector pRC14.
Figure 5:
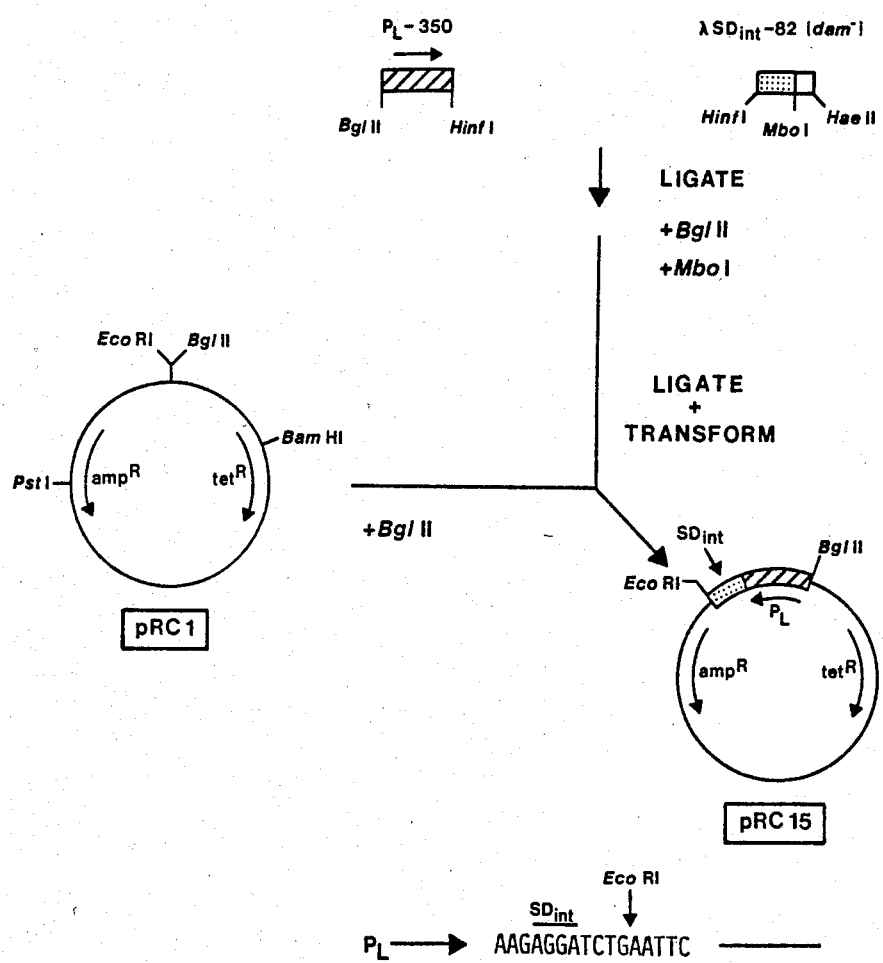
FIG. 5 illustrates the construction of the expression vector pRC15.

To test the utility of the $P_L$ promoter in pRC14 the leukocyte interferon-A (hereinafter sometimes referred to as LeIF-A or LIFA) gene was inserted into a host organism and expressed according to the following procedure. A PstI-EcoR1 fragment from pLeIF A25 [Goeddel, et al, Nature 287, 411 (1980) the source of the LeIF gene] was isolated and ligated to the large EcoR1-PstI fragment isolated from pRC14. The sequence of the junction is shown in FIG. 3. The SD sequence is 5 bases away from the ATG initiation codon. To increase this distance to 9-pRC14/L1FA was digested with EcoR1, the cohesive termini were filled-in with the Klenow fragment off Pol I (+dTTP, dATP), and the blunt-ends religated. The sequence of the resulting junction is shown in FIG. 3 (pRC1410/L1FA). The sequence of the novel hybrid ribosome binding sites utilized in this example are $\overline{AGGAG}AATTC\overline{ATG}$ for pRC14/LIFA and $\overline{AGGAG}AATTAATT\overline{CATG}$ for pRC1410/LIFA (both shown in FIG. 3).

The aforementioned $P_L$ expression plasmids were transformed into a strain of *E. coli* (strain MA210) that carries a defective prophage on its chromosome. The cI repressor gene of the prophage contains a mutation, cIts857, that renders it temperature-sensitive. That is, the repressor is functional from about 30° C. to about 36° C. and inactivated at about 37° C. to about 42° C. This feature provides a convenient mechanism for controlling the $P_L$ promoter. In this case the cells are grown in M9-glucose media at 30° C. to $2-3 \times 10^8$ cells/ml, then shifted to 42° C. for two hours. The cells in the culture are then lysed in 7M Guanidine-HCl and the lysate assayed. When this procedure is followed with pRC1410/LIFA, yields of $10^7$ to $10^8$ units/l of interferon activity are detected in the bacterial extracts or lysate. (see Table 1). The levels of expression in pRC14/LIFA are approximately 10 percent of that obtained in pRC1410/L1FA. pRC15/L1FA yields levels L1FA expression comparable to pRC1410/LIFA (Table 1).

TABLE 1

| E. coli Strain | SD-AUG Distance, bp | LeIF-A Activity Units/ml[d] | (# of exps.) |
| --- | --- | --- | --- |
| MA210(pRC14/LIFA)[a] | 6 | 320–1,280 | (3) |
| MA210(pRC1410/LIFA)[a] | 10 | 7,680–5,360 | (3) |
| MA210(pRC15/LIFA)[a] | 9 | 15,360 | (1) |
| 294(pRC1410/LIFA, pRK248cIts)[b] | 10 | 10,240 | (1) |
| 294(pRC143/LIFA)[c] | 6 | 480 | (1) |
| 294(pRC144/LIFA)[c] | 6 | 480 | (1) |

[a]The cI repressor gene in strain MA210 is present as a defective prophage on the host chromosome and contains the temperature-sensitive mutation cI857.
[b]The cI repressor gene is present as a 2400bp Bgl II insert in pRK248cIts2, a low-copy plasmid which is compatible with derivatives of pBR322.
[c]The cI repressor gene is present as a 2400bp insert at the Bgl II site of pRC14/LIFA in either of the two possible orientations.
[d]The values shown are data obtained from assays on 1:50 dilutions of the bacterial extracts. Thus, 10,000 units/ml converts to $5 \times 10^5$ units/ml of extract or approximately $5 \times 10^4$ units/ml ($5 \times 10^7$ units/L) of culture at $5 \times 10^8$ cells/ml.

EXAMPLE 3

Figure 8:
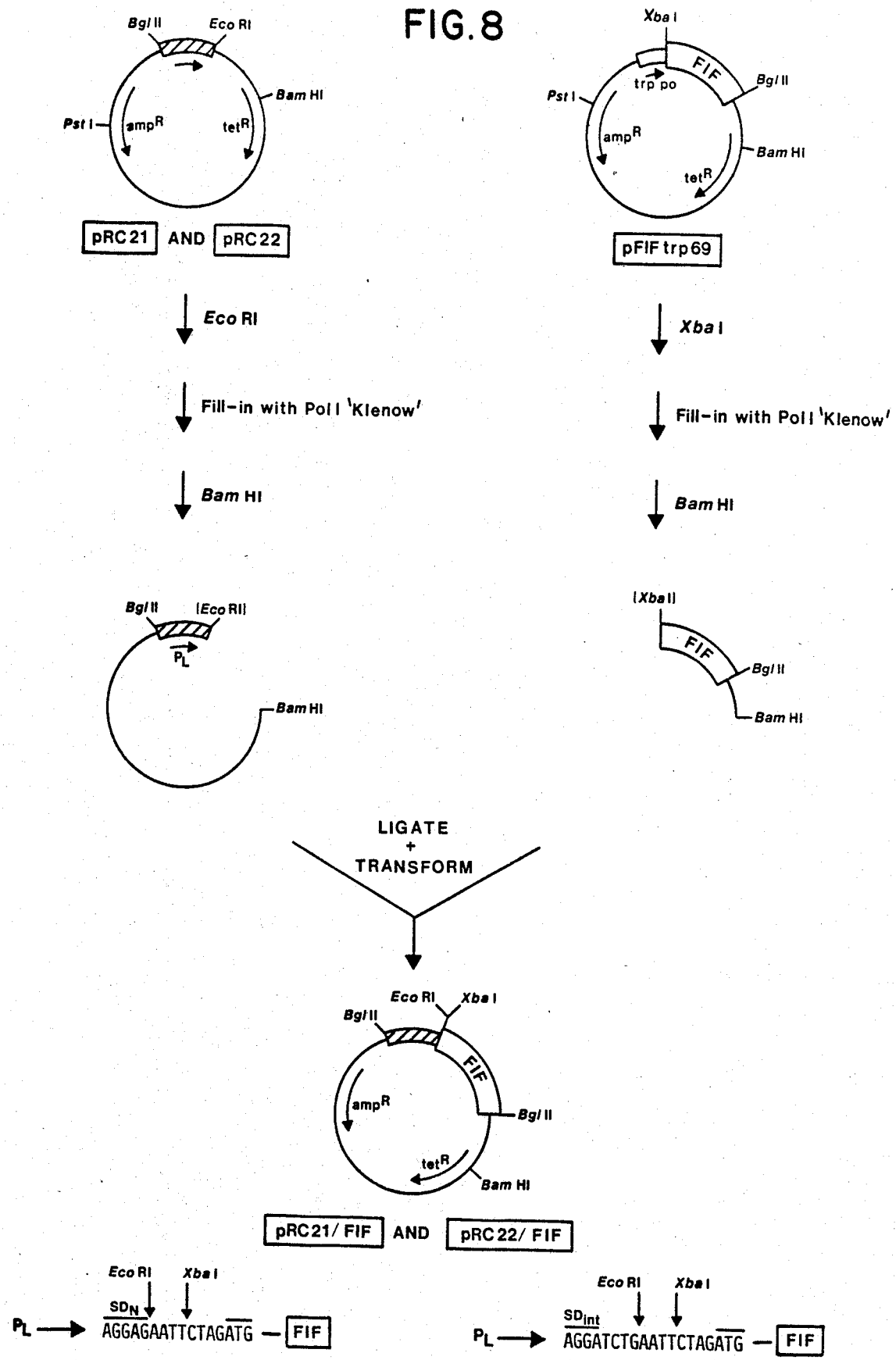
FIG. 8 shows the scheme used to insert the gene coding for fibroblast interferon into pRC21 and pRC22 and the sequences of the resulting promoter-gene junctions.

To test the utility of the $P_L$ promoter the human fibroblast interferon gene (FIF) was inserted into vectors pRC21 and pRC22 as follows (FIG. 8). In separate reactions, pRC21 and pRC22 were digested with EcoR1, the termini were filled-in with Klenow Polymerase I, digested with Bam HI and the large fragment isolated (4.3 Kb). pFIF trp 69 [Goeddel, et al. *Nucleic Acids Res.*, 8, 4057 (1980), the source of the FIF gene] was digested with XbaI, the termini converted to blunt-ends by filling-in with Klenow Pol I, digested with Bam HI, and the smaller fragment (850 bp) containing the FIF gene was isolated. The FIF 850 bp fragment was ligated to the 4.3 Kb $P_L$-containing fragment and the resulting contructions were confirmed by restriction analysis.

To test the ability of the $P_L$-FIF plasmids to produce FIF gene product, E. coli cells transformed with pRC21/FIF and pRC22/FIF were grown at 30° C. in M9-glucose media to a cell density of $2-3 \times 10^8$ cells/ml and induced at 42°, 1 ml samples were taken, cells collected by centrifugation, and resuspended in 7M Guanidine-HCl at $5 \times 10^9$ cells/ml to lyse the cells. Cell debris was removed by centrifugation, and the supernatant was diluted 50-fold prior to being assayed for anti-viral activity. The results are shown in Table 2.

TABLE 2

| E. coli Strain | Incubation/Temperature °C.-Time | FIF Ativity units/ml of extract |
|---|---|---|
| RRl(pRK248cIts,pRC21/FIF) | 30° - control | 0 |
| " | 42° - 0.5 hr. | 1024 |
| " | 42° - 1 hr. | 2048 |
| " | 42° - 2 hr. | 4096 |
| " | 42° - 3 hr. | 256 |
| RRl(pRK248cIts,pRC22/FIF) | 30° - control | 128 |
| " | 42° - 0.5 hr. | 484 |
| " | 42° - 1 hr. | 256 |
| " | 42° - 2 hr. | 2048 |
| " | 42° - 3 hr. | 512 |

EXAMPLE 4

To determine the effect of novel hybrid ribosome binding sites on FIF expression, derivatives of pRC21/FIF and pRC22/FIF were constructed. The combination of the two restriction sites in the linker region of pRC21/FIF and pRC22/FIF (see FIG. 8) provided a means of introducing several modifications in the hybrid RBS. EcoR 1 or Xba 1 were used to cut within the linker region, Klenow Pol I used to fill-in the resulting termini and the blunt-ends were re-ligated, thereby generating the various sequences shown in Table 3. These constructions were tested for FIF expression in a transformed E. coli strain RR1 (pRK248cIts). To test the ability of these $P_L$-FIF plasmids to produce FIF gene product, the following procedure was followed for each culture of cells transformed with a single plasmid variety selected from pRC21/FIF, pRC22/FIF, pRC211/FIF, pRC221/FIF, pRC212/FIF and pRC222/FIF. The cells were grown at 30° in M9-glucose media to a cell density of $2-3 \times 10^8$ cells/ml and induced at 42° for about 120 minutes, 1 ml samples were taken, cells collected by centrifugation, and resuspended in 7M Guanidine-HCl at $5 \times 10^9$ cells/ml to lyse the cells. Cell debris was removed by centrifugation, and the supernatant was diluted 50-fold prior to being assayed for anti-viral activity. The results are shown in Table 3.

EXAMPLE 5

$P_L$-expression vectors were also constructed containing the Immune Interferon (IFI) gene. The source of the IFI gene was pHIT3709, a derivative of pBR322 with a 1100 bp c DNA copy of IFI mRNA inserted at the Pst I site. The coding sequence for IFI present on this insert is:

(5') TGT TAC TGC CAG GAC CCA TAT GTA AAA GAA
GCA GAA AAC CTT AAG AAA TAT TTT AAT GCA GGT
CAT TCA GAT GTA GCG GAT AAT GGA ACT CTT TTC
TTA GGC ATT TTG AAG AAT TGG AAA GAG GAG AGT
GAC AGA AAA ATA ATG CAG AGC CAA ATT GTC TCC
TTT TAC TTC AAA CTT TTT AAA AAC TTT AAA GAT
GAC CAG AGC ATC CAA AAG AGT GTG GAG ACC ATC
AAG GAA GAC ATG GTC AAG TTT TTC AAT AGC
AAC AAA AAG AAA CGA GAT GAC TTC GAA AAG CTG
ACT AAT TAT TCG GTA ACT GAC TTG AAT GTC CAA
CGC AAA GCA ATA CAT GAA CTC ATC CAA GTG ATG
GCT GAA CTG TCG CCA GCA GCT AAA ACA GGG AAG
CGA AAA AGG AGT CAG ATG CTG TTT CGA GGT CGA
AGA GCA TCC CAG—X. (3')

wherein X is TAA, TGA or TAG.

The plasmid pHIT 3709 containing the IFI gene was constructed according to the following procedure.

(i) Isolation of mRNA coding for IFI

Lymphocytes prepared from the human peripheral blood were incubated in RPMI-1640 medium (containing 10% foetal bovine serum) containing 15 ng/ml of 12-O-tetradecanoylphorbol-13-acetate (TPA) and 40 µg/ml of concanavalin A at 37° C. for IFI induction. After 24 hours of incubation, the thus-induced human lymphoytes ($1 \times 10^{10}$ cells) were destructed and denatured in a thioguanidine solution (5M guanidine thiocyanate, 5% mercaptoethanol, 50 mM Tris HCl (pH 7.6), 10 mM EDTA) in a Teflon homogenizer. Then sodium N-lauroyl sarcosinate was added in the concentration of 4% and the mixture after homogenization was layered on 6 ml of 5.7M cesium chloride solution (5.7M cesium chloride, 0.1M EDTA) and centrifuged at 15° C. and 24,000 rpm for 30 hours using a Beckman SW27 rotor to give an RNA precipitate.

This RNA precipitate was dissolved in 0.25% N-lauroyl sarcosinate and then precipitated with ethanol to give 8.3 mg of RNA. This RNA was allowed to be adsorbed, in a high concentration salt solution (0.5M NaCl, 10 mM Tris HCl (pH 7.6), 1 mM EDTA, 0.3% SDS), on an oligo(dT)cellulose column and the poly-(A)-containing mRNA was eluted with a low concentration salt solution (10 mM Tris HCl (pH 7.6), 1 mM EDTA, 0.3% SDS). There was collected 700 µg of mRNA.

TABLE 3

| Plasmid | Sequence of novel hybrid RBS | *SD - ATG Distance | FIF activity units/ml |
|---|---|---|---|
| pRC21/FIF | AGGAGAATTCTAGATG | 8 | 10,240 |
| pRC22/FIF | AGGATCTGAATTCTAGATG | 12 | 2,560 |
| pRC211/FIF | AGGAGAATTAATTCTAGATG | 12 | 5.120 |
| pRC221/FIF | AGGATCTGAATTAATTCTAGATG | 16 | 320 |
| pRC212/FIF | AGGAGAATTCTAGCTAGATG | 12 | 160 |
| pRC222/FIF | AGGATCTGAATTCTAGCTAGATG | 16 | 320 |

*SD sequence consists of the first 4-5 bases indicated with an over-line; ATG is also indicated with an over-line at the end of the sequences.

This mRNA was again precipitated with ethanol, then dissolved in 0.2 ml of a solution (10 mM Tris HCl (pH 7.6), 2 mM EDTA, 0.3% SDS), treated at 65° C. for 2 minutes and fractionated to 22 portions by 10–35% sucrose density gradient centrifugation at 20° C. and 25,000 rpm for 21 hours using a Beckman SW 27 rotor. Aliquots of each fraction were injected into *Xenopas laevis* oocytes and the proteins synthesized were assayed for interferon activity [antiviral activity as assayed by the inhibition test of the cytophathic effect of the vesicular stomatitis virus against human amnion-derived WISH cells (W. E. Stewart, The Interferon System, Springer, Berlin, 1979)]. In this manner, it was revealed that fraction 12 (the sedimentation coefficient being 12–14S) had an activity of 195 units (international IF units) per microgram of RNA. The mRNA in the thus-obtained fraction 12 weighed about 20 μg.

(ii) Synthesis of single-stranded DNA

Using the above mRNA and a reverse transcriptase, 100 μl of a reaction mixture (5 μg of mRNA, 50 μg of oligo(dT), 100 units of reverse transcriptase, 1 mM each of dATP, dCTP, dGTP, and dTTP, 8 mM MgCl$_2$, 50 mM KCl, 10 mM dithiothreitol, 50 mM Tris-HCl (pH 8.3) was incubated at 42° C. for an hour, then deproteinized with phenol, and treated with 0.1N NaOH at 70° C. for 20 minutes for degradation of RNA.

(iii) Synthesis of double-stranded DNA.

The thus-synthesized single-stranded complementary DNA was subjected to reaction in 50 μl of a reaction mixture (the same mixture as above-mentioned except that the mRNA and oligo(dT) were absent) at 42° C. for 2 hours for synthesizing the double-stranded DNA.

(iv) Addition of dC tails

The above double-stranded DNA was treated with nuclease S-1 in 50 μl of a reaction mixture (double stranded DNA, 0.1M sodium acetate (pH 4.5), 0.25M NaCl, 1.5 mM ZnSO$_4$, 60 units S1 nuclease) at room temperature for 30 minutes. The reaction mixture was deproteinized with phenol, the DNA was precipitated with ethanol and subjected to terminal transferase reaction in a mixture (double-stranded DNA, 0.14M potassium cacodylate, 0.3M Tris (base) (pH 7.6), 2 mM dithiothreitol, 1 mM CoCl$_2$, 0.15 mM dCTP, 30 units terminal transferase) at 37° C. for 3 minutes for addition of the double-stranded DNA by about 20 deoxycytidine chains at each 3'-end of the DNA.

This series of reactions gave about 300 ng of a double-stranded deoxycytidine-chain-containing DNA.

(v) Cleavage of *Escherichia coli* plasmid and addition of dG tails

Separately, 10 μg of *Escherichia coli* plasmid pBR322 DNA was treated with restriction enzyme PstI in 50 μl of a reaction mixture [10 μg DNA, 50 mM NaCl, 6 mM Tris HCl (pH 7.4), 6 mM MgCl$_2$, 6 mM 2-mercaptoethanol, 100 μg/ml bovine serum albumin, 20 units PstI] at 37° C. for 3 hours for cleavage at the one PstI recognition site present in the pBR322 DNA, the reaction mixture was then deproteinized with phenol and the DNA was further treated with terminal transferase in 50 μl of a reaction mixture [10 μg DNA, 0.14M potassium cacodylate, 0.3M Tris (base) pH 7.6, 2 mM dithiothreitol, 1 mM CoCl$_2$, 0.15 mM dGTP, 30 units terminal transferase] at 37° C. for 3 minutes for addition of about 8 deoxyguanidine residues at each 3'-end of the above plasmid pBR322 DNA.

(vi) Annealing of cDNA and transformation of *Escherichia coli*

The annealing was effected by heating 0.1 μg of the thus-obtained dC-tailed synthetic double-stranded DNA and 0.5 μg of the above dG-tailed plasmid pBR322 in a solution containing 0.1M NaCl, 50 mM Tris HCl (pH 7.6) and 1 mM EDTA at 65° C. for 2 minutes and then at 45° C. for 2 hours, followed by gradual cooling. The transformation of *Escherichia coli* χ1776 was performed by the method Enea et al. [J. Mol. Biol., 96, 495 (1975)].

(vii) Isolation of plasmid containing cDNA

About 8,500 tetracycline-resistant colonies were thus isolated, and the DNA of each colony was fixed to a nitrocellulose filter [M. Grunstein and D. S. Hogness, Proc. Natl. Acad. Sci. USA, 72, 3961 (1975)].

Separately, based on the amino acid sequence of IFI as reported by D. V. Goeddel et al. [Nature, 295, 503 (1982)], two based sequences

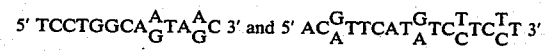

presumably corresponding to amino acids Nos. 1–5 (Cys.Tyr.Cys.Gln.Asp) and amino acids Nos. 77–82 (Lys.Gln Asp.Met.Asn.Val) of said IFI sequence, respectively, were chemically synthesized by the triester method [R. Crea et al., Proc. Natl. Acad. Sci. USA, 75, 5765 (1978)]. These oligonucleotides were treated with T4 polynucleotide kinase in 50 μl of a reaction mixture (0.2 μg oligonucleotide, 50 mM Tris HCl (pH 8.0), 10 mM MgCl$_2$, 10 mM mercaptoethanol, 50 μCi γ-$^{32}$P-ATP, 3 units T4 polynucleotide kinase) at 37° C. for an hour. These oligonucleotides thus labeled with $^{32}$P at the 5'-end were used as probes and annealed with the DNA on the above-mentioned nitrocellulose filter by the method of Lawn et al. [Nucleic Acids Res., 9, 6103 (1981)]. Autoradiography could isolate 4 colonies reactive to the above two oligonucleotide probes.

Plasmid DNAs were isolated from the bacterial cells of each of these colonies by the method of Birnboim and Doly [H. C. Birnboim and J. Doly, *Nucleic Acids Res.*, 1, 1513 (1979)]. The inserts in the plasmid DNAs were excised with the PstI restriction enzyme. From among the isolated plasmids, the one containing the longest cDNA insert was chosen and named "pHIT3709".

Figure 9:
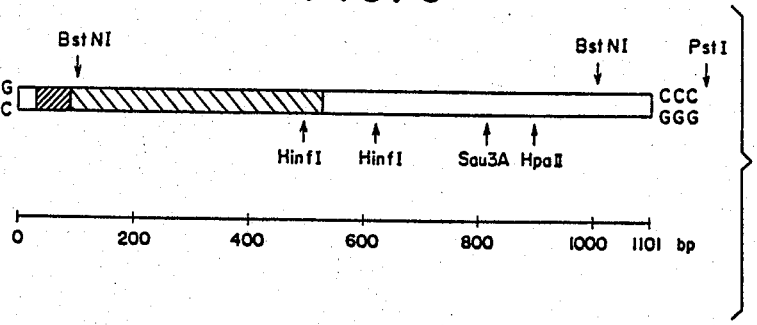
FIG. 9 shows the restriction enzyme cleavage map of the plasmid pHIT3709 as obtained in Example 5 (vii), the portion \\\\\\ indicating the portion coding for the peptide supposed to be the signal peptide and the portion \\\\\\ indicating the portion coding for the IFI polypeptide.
Figure 6:
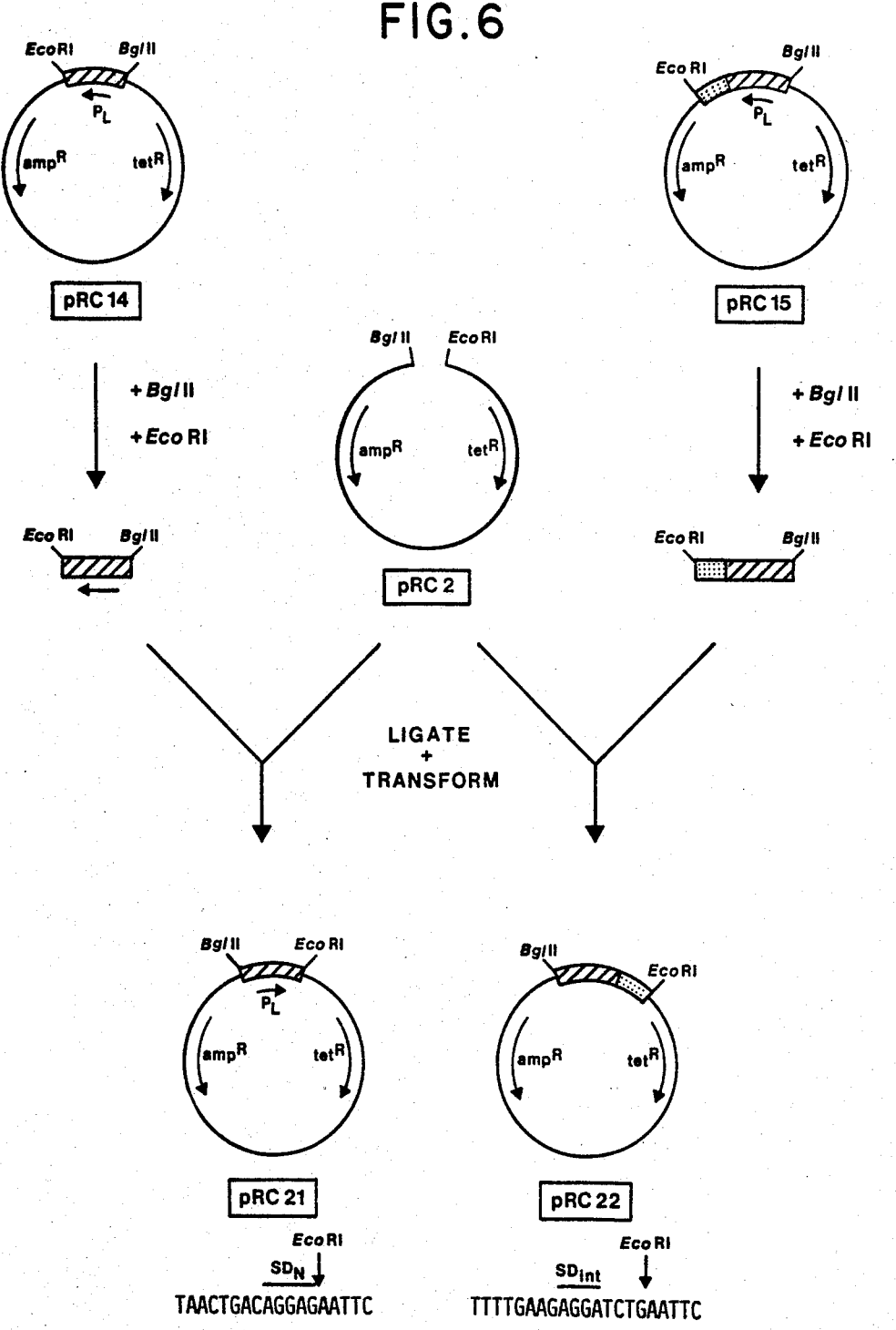
FIG. 6 illustrates the construction of expression vectors pRC21 and pRC22.

The restriction enzyme map of this plasmid is shown in FIG. 9.

The primary structure (base sequence) of the mRNA sequence inserted in the pHIT3709 plasmid was then determined by the dideoxynucleotide synthetic chain termination method and by the Maxam-Gilbert method. Said primary structure was as shown in FIG. 10.

This primary structure is in agreement with that of IFI cDNA as reported by Gray et al. [Nature, 295, 503–508 (1982)] except that the former differs from the latter in one codon; namely, the formers codon for the No. 140 amino acid is CGA, while the latter's is CAA for Gln. The protein determined by this base sequence presumably consists of 166 amino acids whose synthesis is initiated from the No. 30 nucleotide, namely the ATG codon, which is the signal for the start of protein synthesis. The first 20 amino acids probably constitute a signal peptide. The amino acid sequence, too, is different from the IFI reported by Gray et al. with regard to the No. 140 amino acid (Arg in place of Gln).

From the above-mentioned primary structure, it is clear that this plasmid has the entire coding region for the IFI protein. This fact indicates the possibility of making hosts such as *Escherichia coli* produce immune interferon by transfering the DNA sequence inserted in this plasmid to another expression plasmid.

EXAMPLE 6

Figure 11:
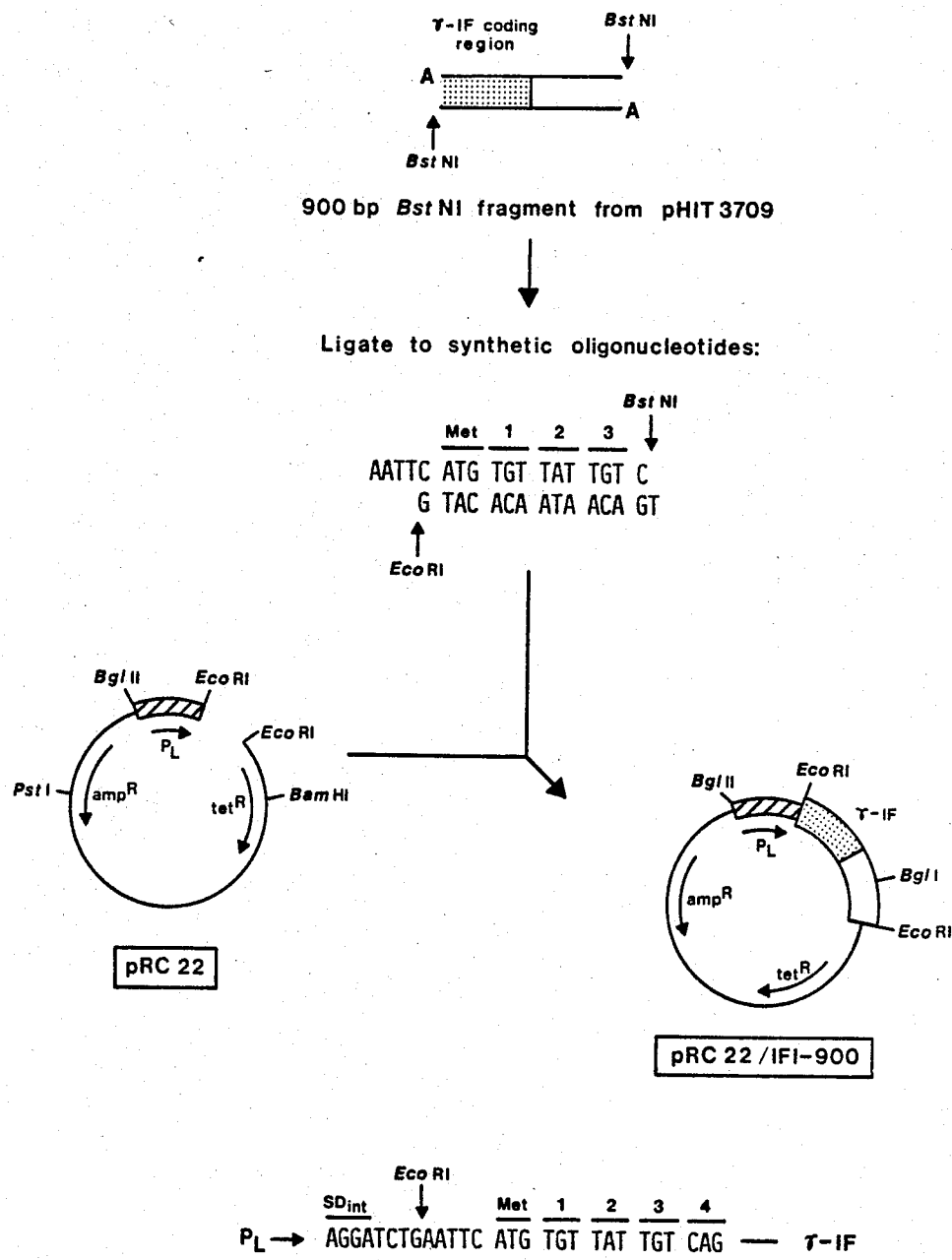
FIG. 11 shows the scheme used to insert the gene coding for immune interferon into pRC22 and the sequence of the promoter-gene junction.

A 900 bp BstN1 fragment was isolated from pH1T 3709 which contains 430 bp of coding sequence for IFI and 470 bp of the 3'-noncoding region. Not present on this fragment are the sequences for the "signal" portion of IFI and the codons for the first 3 amino acids of the presumed mature protein. To restore the three missing codons and to provide an initiating met codon, synthetic oligonucleotides were prepared and ligated to the 900 bp fragment (see FIG. 11). The synthetic segment converted both of the BstN1 termini to EcoR1 termini. The resulting fragment was cloned into vector pRC22 which had been restricted with EcoR1. Orientation of the insert was determined by restriction analysis with Bgl I which cuts within the 3'-noncoding region.

The pRC22 vector containing the IFI gene (denoted pRC22/IFI-900) was sequenced across the promoter-gene junction to assure that all ligation steps occurred as expected. (see FIG. 11)

To test for expression of the IFI gene, strain RRI (pRK248cIts, pRC22/IFI-900) was grown in M9-glucose media at 30°C. to 3–4×10$^8$ cells/ml, then induced at 42° C. for one hour. Prior to induction, additional glucose and casamino acids were added to 1.0 and 0.5 percent, respectively. A 10 ml sample was taken, the cells were collected by centrifugation and resuspended in 0.1 ml of 50 mM Tris (pH7.4), 10 percent sucrose, and the suspension was quick-frozen in a dry ice/ethanol bath. The cells were thawed at 20° C., then transferred to an ice bath. NaCl was added to 100 mM, EDTA to 10 mM, Spermidine to 20 mM, and lysozyme to 200 μg/ml. The mixture was kept on ice for 45 minutes, then incubated at 37° C. for 2 minutes. Cell debris was removed by centrifugation and the supernatant was assayed for IFI anti-viral activity on WISH cells. This initial experiment resulted in a yield of 1280 units of IFI activity per ml of cell extract.

In order to determine the kinetics of induction, the aboe procedure was repeated. One sample was kept at 30° C. as a control, and other samples were taken after induction at 42° C. for 30, 60, 90, 120, and 180 minutes. The samples were processed as described above. The results, shown in Table 4, indicate that at 30° C. no activity is produced and that following induction at 42° C. the amount of activity detected reaches a maximum at around 90 minutes then gradually declines.

TABLE 4

| Strain | Induction conditions Temperature (°C.)-Time | IFI Activity, units/ml |
| --- | --- | --- |
| RR1(pRK248cIts-pRc22/IFI-900) | 30° | 0 |
| " | 42° - 30'* | 120 |
| " | 42° - 60' | 120 |
| " | 42° - 90' | 320 |
| " | 42° - 120' | 160 |
| " | 42° - 180' | 40 |

*' = minutes

Figure 12:
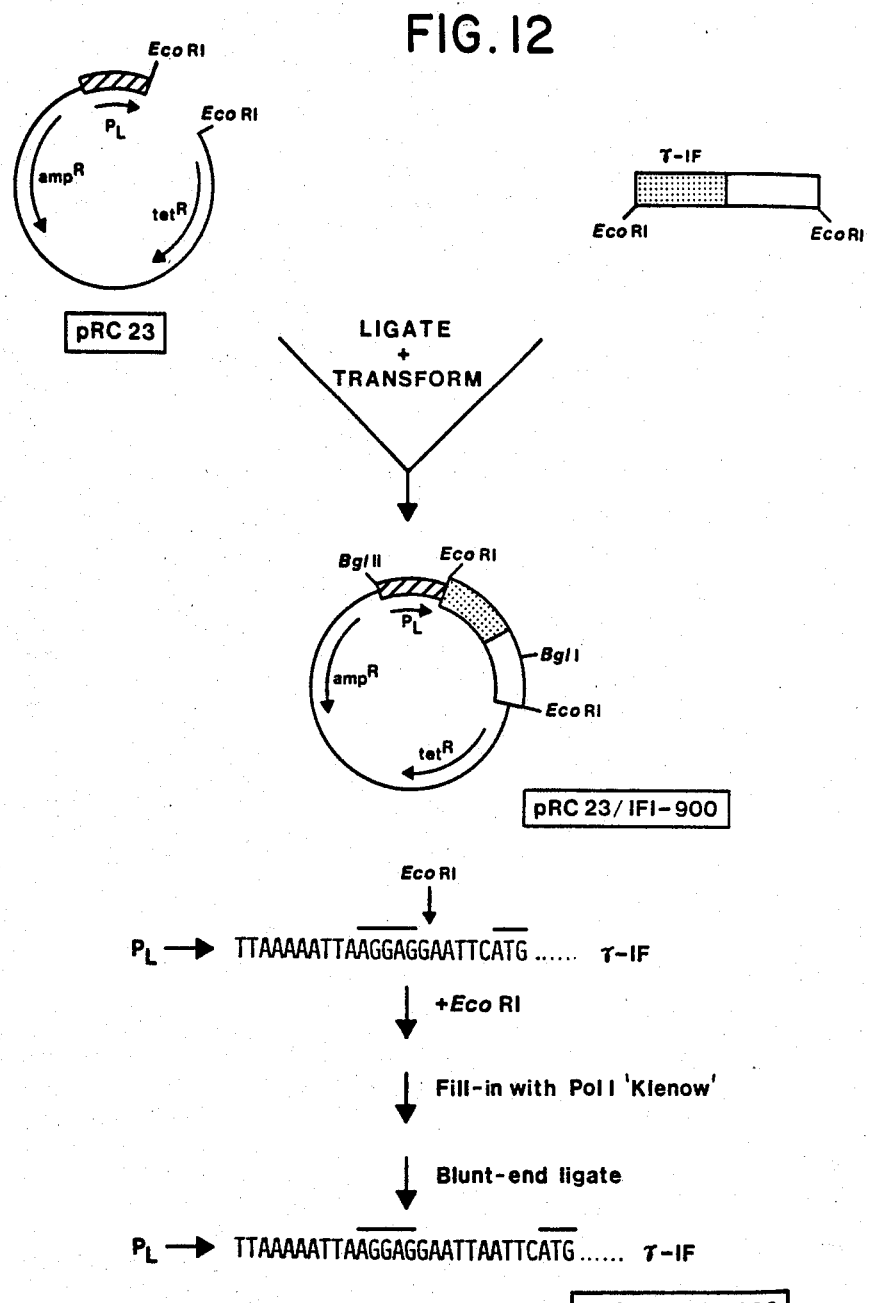
FIG. 12 illustrates the insertion of the immune interferon gene into expression vector pRC23 and the sequence of the promoter gene junction and its modification.

EXAMPLE 7 pRC22/IFI-900 DNA was further restricted with EcoR1 and the 900 bp fragment containing the IFI was isolated and inserted into pRC23 which had been restricted with EcoR1 (see FIG. 12). The resulting construction, pRC23/IFI-900, contained a RBS significantly different from that in pRC22/IFI (compare FIGS. 11 and 12). To test for expression of the IFI gene, strain RRI (pRK248cIts, pRC23/IFI-900) was grown in M9-glucose media at 30° C. to 3–4×10$^8$ cells/ml, then induced at 42° C. for one hour. Prior to induction, additional glucose and casamino acids were added to 1.0 and 0.5 percent, respectively. A 10 ml sample was taken, the cells were collected by centrifugation and resuspended in 0.1 ml of 50 mM Tris (pH7.4), 10 percent sucrose, and the suspension was quick-frozen in a dry ice/ethanol bath. The cells were thawed at 20° C., then transferred to an ice bath. NaCl was added to 100 mM, EDTA to 10 mM, Spermidine to 20 mM, and lysozyme to 200 μg/ml. The mixture was kept on ice for 45 minutes, then incubated at 37° C. for 2 minutes. Cell debris was removed by centrifugation and the supernatant was assayed for IFI anti-viral activity on WISH cells. pRC23/IFI when used to transform *E. coli* strain RR1, produced about four times more IFI activity than pRC22/IFI, as shown in Table 5.

TABLE 5

| Strain | Induction conditions | IFI Activity, units/ml |
| --- | --- | --- |
| RRl(pRK248cIts,pRC22/IFI-900) | 42° - 90'* | 320 |
| RRl(pRK248cIts,pRC23/IFI-900) | 42° - 90' | 1280 |
| RRl(pRK248cIts,pRC231/IFI-900) | 42° - 90' | 640 |

*' = minutes

EXAMPLE 8 pRC23/IFI was further restricted with EcoR1 under conditions that resulted in only one of the two sites being cut. The resulting molecules were then treated with Pol I "Klenow" to fill-in the EcoR1 termini. The blunt-ends were ligated together with T$_4$ DNA ligase and the DNA was used to transform RRI (pRK248cIts). Transformants were screened for the loss of the EcoR1 site at the beginning of the IFI gene and two positives were obtained. One of these, denoted pR231/IFI-900, was used to transform *E. coli* strain RR1 to express IFI. To test for expression of the IFI gene, this strain RRI (pRK248cIts, pRC231/IFI-900) was grown in M9-glucose media at 30° C. to 3–4×10$^8$ cells/ml, then induced at 42° C. for one hour. Prior to induction, additional glucose and casamino acids were added to 1.0 and 0.5 percent, respectively. A 10 ml sample was taken, the cells were collected by centrifugation and resuspended in 0.1 ml of 50 mM Tris (pH7.4), 10 percent sucrose, and the suspension was quick-frozen in a dry ice/ethanol bath. The cells were thawed at 20° C., then transferred to an ice bath. NaCl was added to 100 mM, EDTA to 10 mM, Spermidine to 20 mM, and lysozyme to 200 μg/ml. The mixture was kept on ice for 45 minutes, then incubated at 37° C. for 2 minutes. Cell debris was removed by centrifugation and the supernatant was assayed for IFI anti-viral activity on WISH cells. The results are shown in Table 5.

The modification of pRC23/IFI described was designed to extend the linker region from 6 to 10 bp. The same modification for the LeIF-A expression vector resulted in a 10-20 fold increase in expression. In the case of IFI, a distance of 6 bp appears to be better than 10 bp for expression of IFI.

I claim:

1. An improved expression vector comprising a DNA sequence, said sequence comprising the $P_L$ promoter and operator derived from bacteriophage λ, eucaryotic DNA wherein said eucaryotic DNA carries the DNA base sequence ATG followed by the code for human immune interferon represented by the general formula:

---

Cys Tyr Cys Gln Asp Pro Tyr Val Lys Glu Ala Glu Asn
Leu Lys Lys Tyr Phe Asn Ala Gly His Ser Asp Val Ala
Asp Asn Gly Thr Leu Phe Leu Gly Ile Leu Lys Asn Trp
Lys Glu Glu Ser Asp Arg Lys Ile Met Gln Ser Gln Ile
Val Ser Phe Tyr Phe Lys Leu Phe Lys Asn Phe Lys Asp
Asp Gln Ser Ile Gln Lys Ser Val Glu Thr Ile Lys Glu Asp
Met Asn Val Lys Phe Phe Asn Ser Asn Lys Lys Lys Arg
Asp Asp Phe Glu Lys Leu Thr Asn Tyr Ser Val Thr Asp
Leu Asn Val Gln Arg Lys Ala Ile His glu Leu Ile Gln
Val Met Ala Glu Leu Ser Pro Ala Ala Lys Thr Gln Lys
Arg Lys Arg Ser Gln Met Leu Phe Arg Gly Arg Arg Ala
Ser Gln

--- and a hybrid ribosome binding site linked downstream from said promoter and upstream from the eucaryotic DNA, said hybrid ribosome binding site containing a DNA base sequence represented by the general formula:

TTAAAAATTAAGGAGGAATT.

2. The improved expression vector of claim 1 wherein the operator is $O_L$.

3. The improved expression vector of claim 1 wherein said human immune interferon is coded for by a base sequence represented by the general formula:

(5') TGT TAC TGC CAG GAC CCA TAT GTA AAA GAA
GCA GAA AAC CTT AAG AAA TAT TTT AAT GCA GGT
CAT TCA GAT GTA GCG GAT AAT GGA ACT CTT TTC
TTA GGC ATT TTG AAG AAT TGG AAA GAG GAG AGT
GAC AGA AAA ATA ATG CAG AGC CAA ATT GTC TCC
TTT TAC TTC AAA CTT TTT AAA AAC TTT AAA GAT
GAC CAG AGC ATC CAA AAG AGT GTG GAG ACC ATC
AAG GAA GAC ATG AAT GTC AAG TTT TTC AAT AGC
AAC AAA AAG AAA CGA GAT GAC TTC GAA AAG CTG
ACT AAT TAT TCG GTA ACT GAC TTG AAT GTC CAA
CGC AAA GCA ATA CAT GAA CTC ATC CAA GTG ATG
GCT GAA CTG TCG CCA GCA GCT AAA ACA GGG AAG
CGA AAA AGG AGT CAG ATG CTG TTT CGA GGT CGA

-continued

AGA GCA TCC CAG—X. (3')

wherein X is TAA, TGA or TAG.

4. The improved expression vector of claim 1 wherein said vector further comprises a mutant cI repressor gene derived from λ bacteriophage which mutant gene codes for a temperature sensitive repressor protein.

5. The improved expression vector of claim 4 wherein the temperature sensitive repressor protein is functional from about 30° C. to about 36° C.

6. A bacterial host transformed with the expression vector according to any of the claims 1 or 2.

7. A host according to claim 6, wherein said host is *Escherichia coli*.

8. A method for producing human immune interferon comprising:
   (a) transforming a bacterial host organism with the expression vector of any one of claims 1, 2, 3, 4 and 5,
   (b) lysing the human immune interferon producing bacterial organism of step (a) and
   (c) recovering human immune interferon from the resultant lysate.

9. The method of claim 8 wherein immediately prior to lysing the temperature of the bacterial host organism is raised to a point at which the temperature sensitive repressor protein is inactivated.

10. The method of claim 9 wherein the temperature at which the temperature sensitive repressor protein is completely inactivated is about 37° C. to about 42° C.

11. The improved expression vector of claim 1 wherein said hybrid ribosome binding site contains a DNA base sequence represented by the general formula:

TTAAAAATTAAGGAGGAATTC.

12. The method of claim 10 wherein the inteferon is recovered chromatographically.

13. The method of claim 12 wherein the chromatography is antibody affinity chromatography.

14. The improved expression vector of claim 1 wherein said hybrid ribosome binding site contains a DNA base sequence represented by the general formula:

TTAAAAATTAAGGAGGAATTAATTC.

15. The method of claim 8 wherein the lysing procedure is performed enzymatically.

* * * * *